United States Patent
Koros et al.

(10) Patent No.: US 7,160,356 B2
(45) Date of Patent: Jan. 9, 2007

(54) DITHIOLENE FUNCTIONALIZED POLYMER MEMBRANE FOR OLEFIN/PARAFFIN SEPARATION

(75) Inventors: William J. Koros, Atlanta, GA (US); Ryan L. Burns, Yorktown Heights, NY (US)

(73) Assignee: Board of Regents, The University of Texas System, Austin, TX (US)

( * ) Notice: Subject to any disclaimer, the term of this patent is extended or adjusted under 35 U.S.C. 154(b) by 436 days.

(21) Appl. No.: 10/824,772

(22) Filed: Apr. 15, 2004

(65) Prior Publication Data

US 2005/0000899 A1    Jan. 6, 2005

Related U.S. Application Data

(60) Provisional application No. 60/463,008, filed on Apr. 15, 2003.

(51) Int. Cl.
*B01D 53/22* (2006.01)
*B01D 61/00* (2006.01)
*B01D 69/00* (2006.01)
*B01D 71/56* (2006.01)

(52) U.S. Cl. .................. 95/50; 96/14; 210/500.28; 210/500.38

(58) Field of Classification Search ............ 95/43, 95/45, 50; 96/4, 14; 210/650, 500.27, 500.28, 210/500.38, 500.39
See application file for complete search history.

(56) References Cited

U.S. PATENT DOCUMENTS

| | | |
|---|---|---|
| 2,894,988 A | 7/1959 | Cryer |
| 3,518,232 A | 6/1970 | Bell |
| 3,657,190 A | 4/1972 | Hughes et al. |
| 3,792,024 A | 2/1974 | Saferstein |
| 3,817,386 A | 6/1974 | Frost et al. |
| 3,878,109 A | 4/1975 | Ikeda et al. |
| 4,113,683 A | 9/1978 | Kalnin et al. |
| 4,717,394 A | 1/1988 | Hayes |
| 4,755,192 A | 7/1988 | Koros et al. |
| 4,902,422 A | 2/1990 | Pinnau et al. |
| 4,944,880 A | 7/1990 | Ho et al. |
| 4,946,594 A | 8/1990 | Thaler et al. |
| 4,990,275 A | 2/1991 | Ho et al. |
| 4,997,906 A | 3/1991 | Thaler et al. |
| 5,074,891 A | 12/1991 | Kohn et al. |

(Continued)

FOREIGN PATENT DOCUMENTS

EP    0 446 947    5/1995

(Continued)

OTHER PUBLICATIONS

Bai et al., "*Metal-ion mediated separation of propylene from propane using PPO membranes*," Journal of Membrane Science, 147(1998) pp. 131-139.

(Continued)

*Primary Examiner*—Frank M. Lawrence
(74) *Attorney, Agent, or Firm*—Meyertons, Hood, Kivlin, Kowert & Goetzel, P.C.; Eric B. Meyertons

(57) ABSTRACT

A polymeric composite may be used for forming fluid separation membranes. The membranes may be formed from polyimide, polyamide or poly (pyrrolone-imide) materials. Polyamides may be formed by the condensation of a tetraamine, a tetraacid, and a diamine. Polyimides and poly (pyrrolone-imides) may be formed by the cyclization of a polymer precursor. A polymeric composite may include a dithiolene or a mixture of dithiolenes. A polymer matrix incorporating dithiolenes may exhibit an olefin/paraffin solubility selectivity. A solubility selectivity may be between about 1.1 and about 2.0.

41 Claims, 3 Drawing Sheets

U.S. PATENT DOCUMENTS

| | | | |
|---|---|---|---|
| 5,075,419 | A | 12/1991 | Vora et al. |
| 5,120,825 | A | 6/1992 | Vora et al. |
| 5,262,056 | A | 11/1993 | Koros et al. |
| 5,288,304 | A | 2/1994 | Koros et al. |
| 5,425,801 | A | 6/1995 | Prasad |
| 5,430,218 | A | 7/1995 | Miller et al. |
| 5,593,157 | A | 1/1997 | Koros et al. |
| 5,599,380 | A | 2/1997 | Koros |
| 5,972,080 | A | 10/1999 | Nagata |
| 6,296,755 | B1 | 10/2001 | Wang et al. |
| 6,299,669 | B1 | 10/2001 | Koros et al. |
| 6,503,295 | B1 | 1/2003 | Koros et al. |
| 6,562,110 | B1 | 5/2003 | Koros et al. |
| 6,565,631 | B1 | 5/2003 | Koros et al. |
| 6,585,802 | B1 | 7/2003 | Koros et al. |
| 6,602,415 | B1 | 8/2003 | Koros et al. |
| 6,755,900 | B1 | 6/2004 | Koros et al. |
| 2003/0225296 | A1* | 12/2003 | Mueller-Westerhoff et al. ............... 556/136 |

FOREIGN PATENT DOCUMENTS

| | | |
|---|---|---|
| EP | 0 820 805 | 1/1998 |

OTHER PUBLICATIONS

Bell et al., "Synthesis and Properties of Polyimidazopyrrolones," Journal of Polymer Science: Part A1 5(1967) pp. 3043-3060.

Bondi, "Catalog of Molecular Properties" in Physical Properties of Molecular Crystals, Liquid and Glasses, 1968, pp. 450-483 (Wiley, New York, NY).

Coleman, "Isomers of Fluorine Containing Polyimides for Gas Separation Membranes," Ph. D dissertation, University of Texas at Austin TX 1992. 252 pages.

Freeman, "Basis of Permeability/Selectivity Tradeoff Relations in Polymeric Gas Separation Membranes", Macromolecules, 32(1999) pp. 375-380.

Ilinich et al., "Separation of ethylene and ethane over polyphenyleneoxides membranes: transient increase of selectivity", Journal of Membrane Sciences, 82(1993) pp. 149-155.

Ito et al., "Permeation of Propane and Propylene through Cellulosic Polymer Membranes," Journal of Applied Polymer Science, 38(1989) pp. 483-490 (Wiley, New York, NY).

Kim et al., "Relationship Between Gas Separation Properties and Chemical Structures in a Series of Aromatic Polyimides", Journal of Membrane Science, 37(1988) pp. 45-62 (Elsevier, Amsterdam).

Kim et al., "Advanced Gas Separation Membrane Materials: Rigid Aromatic Polyimides," Separation Science and Technology, 23:12-13(1988) pp. 1611-1626 (Dekker, Inc.).

Kim, "Gas Sorption and Permeation in a Series of Aromatic Polyimides," Ph.D. dissertation, University of Texas at Austin, TX, 1988, 159 pages.

Koros et al., "Gas Separation Membrane Material Selection Criteria: Weakly and Strongly Interacting Feed Component Situations," Polymer Journal, 23:5 (1991) pp. 481-490.

Koros et al., "$CO_2$ Sorption in Poly(ethylene Terephthalate) above and below the Glass Transition," Journal of Polymer Science: Polymer Physics, 16(1978) pp. 1947-1963 (Wiley, New York, NY).

Koros et al., "Sorption and Transport of Various Gases in Polycarbonate," Journal of Membrane Science, 2(1977) pp. 165-190 (Elsevier, Amsterdam).

Lee et al., "Separation of propylene and propane by polyimide hollow-fiber membrane module," Journal of Membrane Science, 73(1992) pp. 37-45 (Elsevier, Amsterdam).

Olson et al., "Polarographic Study of Coordination Compounds with Delocalized Ground States. Substituent Effects in Bis- and Trisdithiodiketone Complexes of Transition Metals," Journal of the American Chemical Society, 88:21(1966) pp. 4876-4882 (American Chemical Society, OH).

Park et al., "Facilitated transport of olefin through solid PAAm and PAAm-graft composite membranes with silver ions," Journal of Membrane Science, 183(2001) pp. 163-170 (Elsevier, Amsterdam).

Petropoulos, "Quantitative Analysis of Gaseous Diffusion in Glassy Polymers," Journal of Polymer Science: Part A-2, 8(1970) pp. 1797-1801 (Wiley, New York, NY).

Pinnau et al., "Solid polymer electrolyte composite membranes for olefin/paraffin separation," Journal of Membrane Science, 184(2001) pp. 39-48 (Elsevier, Amsterdam).

Robeson, "Correlation of separation factor versus permeability for polymeric membranes," Journal of Membrane Science, 62(1991) pp. 165-185 (Elsevier, Amsterdam).

Scott et al., "Polyimidazopyrrolone Reverse Osmosis Membranes," Polymer Letters, 8(1970) pp. 563-571.

Shimazu et al., "Relationships between the Chemical Structures and the Solubility, Diffusivity, and Permselectivity of Propylene and Propane in 6FDA-Based Polyimides," Journal of Polymer Science: Part B: Polymer Physics, 38(2000), pp. 2525-2536 (Wiley, New York, NY).

Shimazu et al., "Relationships Between Chemical Structures and Solubility, Diffusivity, and Permselectivity of 1,3-Butadiene and n-Butane in 6FDA-Based Polyimides," Journal of Polymer Science: Part B: Polymer Physics, 37(1999) pp. 2941-2949.

Staudt-Bickel et al., "Olefin/paraffin separation with 6FDA-based polyimide membranes," Journal of Membrane Science, 170(2000) pp. 205-214 (Elsevier, Amsterdam).

Steel, "Carbon Membranes for Challenging Gas Separations," Ph.D. dissertation, The University of Texas at Austin TX, 2000, 199 pages.

Tanaka et al., "Permeation and separation properties of polyimide membranes to olefins and paraffins." Journal of Membrane Science, 121(1996) pp. 197-207 (Elsevier, Amsterdam).

Van Krevelen et al., "Volumetric Properties" in Properties of Polymers: Their Estimation and Correlation with Chemical Structure, 2nd Edition, Elsevier, Amsterdam, 1976, pp. 51-79.

Vieth et al., "Dual Sorption Theory," Journal of Membrane Science, 1(1976), pp. 177-220 (Elsevier, Amsterdam).

Walker, "Synthesis and Characterization of Polypyrrolones for Gas Separation Membranes," Ph.D. dissertation, The University of Texas at Austin, Texas, 1993, 188 pages.

Walker et al., "Transport characterization of a polypyrrolone for gas separations," Journal of Membrane Science, 55(1991) pp. 99-117 (Elsevier, Amsterdam).

Wang et al., "Toward Separation and Purification of Olefins Using Dithiolene Complexes: An Electrochemical Approach," Science, 291(2001) pp. 106-109.

Zimmerman, "Advanced Gas Separation Membrane Materials: Hyper Rigid Polymers and Molecular Sieve-Polymer Mixed Matrices," Ph.D. dissertation, The University of Texas at Austin, TX, 1998, 322 pages.

Burns, "Investigation of Poly(pyrrolone-imide) Materials for the Olefin/Paraffin Separation," Ph.D. dissertation, The University of Texas at Austin, TX, 2002, 213 pages.

European Patent Office, "International Search Report," International Application No. PCT/US02/03962 mailed Aug. 27, 2003, 7 pages.

European Patent Office, "International Preliminary Examination Report" for International Application No. PCT/US02/03962 mailed Sep. 19, 2003, 8 pages.

Bell et al., "Polyimidazopyrrolones: A New Route to Ladder Polymers," Polymer Letters, 1965, vol. 3, pp. 977-984.

Berlin et al., "Thermostable Polymers from Dianhydrides of Aromatic Tetracarboxylic Acids and Tetra-amines," Russian Chemical Reviews, 1971, vol. 40(3), pp. 284-300.

Berry et al., "Cryoscopy on Sulfuric Acid Solutions of a Heterocyclic Polymer (BBB) and Related Compounds" Journal of Polymer Science: Polymer Physics Edition, 1974, vol. 12, pp. 2253-2266 (Wiley, New York, NY).

Bruma et al., "Synthesis of a Pyrrolone-Type Polymer Containing Anthraquinone Units in Molten Antimony Trichloride," Journal of Polymer Science: Polymer Chemistry Edition, 1974, vol. 12, pp. 2385-2389 (Wiley, New York, NY).

Colson et al., "Polybenzoylenebenzimidazoles," Journal of Polymer Science: Part A-1, 1966, vol. 4, pp. 59-70.

Dawans et al., "*Polymers from ortho Aromatic Tetraamines and Aromatic Dianhydrides*," Journal of Polymer Science: Part A, 1965, vol. 3, pp. 3549-3571.

Foster et al., "*Polybenzimidazoles. IV. Polybenzimidazoles Containing Aryl Ether Linkages*," Journal of Polymer Science: Part A, 1965, vol. 3, pp. 417-412.

Sulzberg et al., "*Synthesis and Polymerization of a Dinitrobisphenol A: A new Polycarbonate Synthesis*," Polymer Letters, 1969, vol. 7, pp. 185-191.

European Patent Office Communication, Search Report for EP application No. EP 0400 8852, mailed Jul. 22, 2004, (6 pages).

Allison et al., "*Multicarrier Transport: Coupled Transport of Electrons and Metal Cations Mediated by an Electron Carrier and a Selective Cation Carrier*," Journal of American Chemical Society, 1979, pp. 1333-1334.

Burns et al., "*Defining the challenges for $C_3H_6/C_3H_8$ separation using polymeric membranes*," Journal of Membrane Science, 2003, vol. 211, pp. 259-309. (Elsevier).

Fan et al., "*How Electron Flow Controls the Thermochemistry of the Addition of Olefins to Nickel Dithiolenes: Predictions by Density Functional Theory*," Journal of American Chemical Society, 2002, pp. 12076-12077.

Bickel, et al. "*Olefin/paraffin gas separations with 6FDA-base polyimide membranes*," Journal of Membrane Science, 2000, vol. 170, pp. 105-214.

Hashimoto, "*Selective separation of olefins using dithiolene complexes. Electrochemical control*," retrieved from STN, Chemical Abstracts Service, Database CHEMABS (online) Columbus, Ohio, abstract, 2001 (1 page).

\* cited by examiner

DITHIOLENE FUNCTIONALIZED POLYMER MEMBRANE FOR OLEFIN/PARAFFIN SEPARATION

PRIORITY CLAIM

This application claims priority to U.S. Provisional Patent Application No. 60/463,008 entitled "DITHIOLENE FUNCTIONALIZED POLYMER MEMBRANE FOR OLEFIN/PARAFFIN SEPARATION" filed Apr. 15, 2003, which is incorporated herein by reference.

BACKGROUND OF THE INVENTION

1. Field of the Invention

The present invention generally relates to polymeric membranes that exhibit gas selectivity. Specifically, rigid polymeric membranes that exhibit an olefin/paraffin selectivity are described.

2. Description of the Related Art

The separation of one or more gases from a multicomponent mixture of gases is necessary in a large number of industries. Such separations currently are undertaken commercially by processes such as cryogenics, pressure swing adsorption, and membrane separations. In certain types of gas separations, membrane separations have been found to be economically more viable than other processes.

In a pressure-driven gas membrane separation process, one side of the gas separation membrane is contacted with a multicomponent gas mixture. Certain of the gases of the mixture permeate through the membrane faster than the other gases. Gas separation membranes thereby allow some gases to permeate through them while serving as a relative barrier to other gases. The relative gas permeation rate through the membrane is a property of the membrane material composition and its morphology.

It has been suggested in the prior art that the intrinsic permeability of a polymer membrane is a function of both gas diffusion through the membrane, controlled in part by the packing and molecular free volume of the material, and gas solubility within the material. Selectivity may be determined by the ratio of the permeabilities of two gases being separated by a material.

Transport of gases in polymers and molecular sieve materials occurs via a well known sorption-diffusion mechanism. The permeability coefficient ($P_A$) of a particular gas is the flux ($N_A$) normalized to the pressure difference across the membrane ($\Delta P_A$), and the membrane thickness (l).

$$P_A = N_A \frac{l}{\Delta p_A} \quad (1)$$

The permeability coefficient of a particular penetrant gas is also equal to the product of the diffusion coefficient ($D_A$) and the solubility coefficient ($S_A$).

$$P_A = D_A S_A \quad (2)$$

The permselectivity ($\alpha_{A/B}$) of a membrane material (also ideal selectivity) is the ratio of the permeability coefficients of a penetrant pair for the case where the downstream pressure is negligible relative to the upstream feed pressure. Substituting equation (2), the ideal permselectivity is also a product of the diffusivity selectivity and solubility selectivity of the particular gas pair.

$$\alpha_{A/B} = \frac{P_A}{P_B} = \frac{D_A}{D_B} \cdot \frac{S_A}{S_B} \quad (3)$$

The variation of gas permeability with pressure in glassy polymers is often represented by the dual mode model. Petropulos (1970); Vieth, et al. (1976); Koros, et al. (1977). The model accounts for the differences in gas transport properties in an idealized Henry's law and Langmuir domains of a glassy polymer, $$P = k_D D_D + \frac{C'_H D_H b}{1 + bp} \quad (4)$$

where $k_D$ is the Henry's law constant, $C'_H$ is the Langmuir capacity constant, p is pressure, and b is the Langmuir affinity constant. This model can be further extended to mixed gas permeability:

$$P_A = k_{DA} D_{DA} + \frac{C'_{HA} b_A D_{HA}}{1 + b_A p_A + b_B p_B} \quad (5)$$

where $p_A$ and $p_B$ are the partial pressures of gasses A and B respectively. This model is valid for a binary gas mixture of components A and B, and it only accounts for competitive sorption.

The temperature dependence of permeability for a given set of feed partial pressures is typically represented by an Arrhenius relationship:

$$P = P_o \exp\left[\frac{-E_p}{RT}\right] \quad (6)$$

where $P_o$ is a pre-exponential factor, $E_p$ is the apparent activation energy for permeation, T is the temperature of permeation in Kelvin, and R is the universal gas constant. The permeability can further be broken up into temperature dependent diffusion and sorption coefficients from equation (2). The temperature dependence of the penetrant diffusion coefficient can also be represented by an Arrhenius relationship:

$$D = D_o \exp\left[\frac{-E_d}{RT}\right] \quad (7)$$

Again $D_o$ is a pre-exponential factor, and $E_d$ is the activation energy for diffusion. The activation energy for diffusion represents the energy required for a penetrant to diffuse or "jump" from one equilibrium site within the matrix to another equilibrium site. The activation energy is related to the size of the penetrant, the rigidity of the polymer chain, as well as polymeric chain packing. The temperature dependence of sorption in polymers may be described using a thermodynamic van't Hoff expression:

$$S = S_o \exp\left[\frac{-H_s}{RT}\right] \quad (8)$$

where $S_o$ is a pre-exponential factor, and $H_s$ is the apparent heat of sorption as it combines the temperature dependence of sorption in both the Henry's law and Langmuir regions.

From transition state theory the pre-exponential for diffusion can be represented by $$D_o = e\lambda^2 \frac{kT}{h} \exp\left[\frac{S_d}{R}\right] \quad (9)$$

Here, $S_d$ is the activation entropy, $\lambda$ is the diffusive jump length, k is Boltzmann's constant, and h is Planck's constant. Substituting (9) into (3) (neglecting small differences in the jump length of similarly sized penetrants) results in the diffusive selectivity as the product of energetic and entropic terms:

$$\frac{D_A}{D_B} = \exp\left[\frac{-\Delta E_{d,A,B}}{RT}\right]\exp\left[\frac{\Delta S_{d,A,B}}{R}\right] \quad (10)$$

The diffusivity selectivity is determined by the ability of the polymer to discriminate between the penetrants on the basis of their sizes and shapes, and is governed primarily by intrasegmental motions and intersegmental packing. The diffusive selectivity will be based on both the difference in activation energy for both penetrants, $\Delta E_d$, as well as the difference in activation entropy for both penetrants, $\Delta S_d$.

Much of the work in the field has been directed to developing membranes that optimize the separation factor and total flux of a given system. It is disclosed in U.S. Pat. No. 4,717,394 to Hayes that aromatic polyimides containing the residue of alkylated aromatic diamines are useful in separating a variety of gases. Moreover, it has been reported in the literature that other polyimides, polycarbonates, polyurethanes, polysulfones and polyphenyleneoxides are useful for like purposes. U.S. Pat. No. 5,599,380 to Koros, herein incorporated by reference, discloses a polymeric membrane with a high entropic effect. U.S. Pat. No. 5,262,056 to Koros et al., herein incorporated by reference, discloses polyamide and polypyrrolone membranes for fluid separation.

U.S. Pat. No. 5,074,891 to Kohn et al. discloses certain polyimides with the residuum of a diaryl fluorine-containing diamine moiety as useful in separation processes involving, for example, $H_2$, $N_2$, $CH_4$, CO, $CO_2$, He and $O_2$. By utilizing a more rigid repeat unit than a polyimide, however, even greater permeability and permselectivity are realized. One example of such a rigid repeat unit is a polypyrrolone.

Polypyrrolones as membrane materials were proposed and studied originally for the reverse osmosis purification of water by Scott et al. (1970). The syntheses, permeabilities, solubilities and diffusivities of polypyrrolones and polyimides have been described in (Walker and Koros (1991); Koros and Walker (1991); Kim et al. (1988a, b); Kim (1988c); Coleman (1992)). Membranes that are composed of the polyamide and polypyrrolone forms of hexafluoroisopropylidene-bisphthalic anhydride are disclosed in U.S. Pat. No. 5,262,056 which is incorporated herein by reference.

In the petrochemical industry, one of the most important processes is the separation of olefin and paraffin gases. Olefin gases, particularly ethylene and propylene, are important chemical feed stocks. Various petrochemical streams contain olefins and other saturated hydrocarbons. These streams typically originate from a catalytic cracking unit. Currently, the separation of olefin and paraffin components is done using low temperature distillation. Distillation columns are normally around 300 feet tall and contain over 200 trays. This is extremely expensive and energy intensive due to the similar volatilities of the components.

It is estimated that $1.2 \times 10^{14}$ BTU per year are used for olefin/paraffin separations. This large capital expense and exorbitant energy cost have created incentive for extensive research in this area of separations. Membrane separations have been considered as an attractive alternative. Some examples of membranes that exhibit attractive selectivity under mild conditions have been reported. (Tanaka et al. (1996); Staudt-Bickel and Koros (2000); Ilinitch et al. (1993); Lee et al. (1992); Ito et al. (1989)). In practice, high propylene/propane temperatures and pressures are preferred for economical processing. Thus, a polymer membrane that showed enhanced propylene/propane selectivity under increasingly demanding processing conditions would be of particular value. Recent gas transport studies aimed at improving current membrane performance have examined glassy polymers focusing mainly on polyimides. Tanaka et al. (1996) have reported one of the highest performance polyimides to date. This data along with other literature data has been used to construct a preliminary propane/propylene "upper bound" trade off curve between gas permeability and selectivity, as shown in FIG. 1 (Tanaka et al. (1996); Staudt-Bickel and Koros (2000); Ilinitch et al. (1993); Lee et al. (1992); Ito et al. (1989); Steel (2000)). The conditions chosen for the upper bound curve are 2–4 atm feed pressure and 35–55° C. The propane/propylene trade off curve is less defined at this point in comparison to $O_2/N_2$ and $CO_2/CH_4$ "upper bound" curves defined previously (Robeson (1991)).

According to Freeman's analysis, the "upper bound" for conventional polymers used for gas separations can be shown to follow equation 11:

$$\alpha_{A/B} = (\beta_{A/B})/(P_A^{\lambda_{A/B}}) \quad (11)$$

The parameter, $\lambda_{A/B}$ can be shown to be proportional to the square of the size difference of the two gas molecules, $(d_A/d_B)^2$. Consequently, this parameter is difficult to manipulate through materials engineering. Therefore, according to the theory, in order to "move" the upper bound limit, the strategy must be to increase the $\beta$ parameter, which can be shown to be proportional to the value, $S_A$ $(S_A/S_B)^\lambda$, as well as a parameter f, which relates to the interchain spacing. Previous work has attempted to increase the diffusivity selectivity through an increase in the chain rigidity by using polypyrrolone materials. However, another approach to "elevating" the upper bound is to improve the solubility of the "fast gas" (i.e., $C_3H_6$ in this case), thereby increasing the solubility selectivity, and increasing $\beta$. The solubility of an olefin in a polymeric material is a parameter that can be engineered through the use of $\pi$-bonding interactions.

Previous researchers have examined the viability of fixed site facilitated membranes for the separation of olefins from paraffins. Typically, Group I-B metals, such as silver, are dissolved in polymer membranes in a salt form. Examples of silver salts conventionally used include $AgBF_4$ and $AgNO_3$. Once dissolved in the polymer, the salt dissociates, and the silver cation is able to form a complex with an olefin due to the interaction of the $\pi$-orbital of the olefin with the $\sigma$ and $\pi$-orbital of the metal.

These fixed site facilitated membranes still have a major practical problem, however, due to the poor chemical stability of the metal-olefin complex. This metal-olefin complex is easily poisoned by small amounts of hydrogen gas, carbon monoxide, acetylene, or hydrogen sulfide in the feed stream. Silver ions also have the potential to react with acetylene to form an explosive silver acetylide salt.

A search has been ongoing to find a material which can form a π-bond complex with olefins, while still maintaining stability in the presence of the aforementioned impurity gases. An additional constraint is that the material should be able to dissolve in state-of-the-art polyimide membranes. The overall strategy is to maintain the high diffusivity selectivity ($D_A/D_B$) already available with polyimides, and enhance this diffusivity selectivity by a factor of the improved solubility selectivity ($S_A/S_B$). For a conventional polyimide with a $C_3H_6/C_3H_8$ selectivity of 15, a small increase in the solubility selectivity from 1.0 to 2.0 would double the overall $C_3H_6/C_3H_8$ selectivity to a value of 30, as well as doubling the $C_3H_6$ flux.

SUMMARY

Described herein is a polymeric fluid separation membrane. In one embodiment, the fluid separation membrane may be formed from the reaction product of a tetraacid compound and a diamine. The initial resulting product is a polyamide. This polyamide may be used to form a fluid separation membrane. The polyamide may be thermally or chemically cyclized to form a polyimide. The polymer matrix of the fluid separation membrane may also include a dithiolene.

In an embodiment where dithiolenes are included within the polymer matrix, rigid polymeric membranes that exhibit an olefin/paraffin solubility selectivity may result. Dithiolenes may be added to a polymer formed by reacting a tetraacid compound with a diamine, a tetraamine, or a mixture of diamines and tetraamines. Dithiolenes may be added to any polymer matrix such that the dithiolenes are substantially homogeneously dispersed within the polymer matrix.

The fluid separation membrane may be formed by adding a tetraacid compound to an amine mixture. The amine mixture may include tetraamines and diamines. The tetraamine to diamine ratio may be between about 5:95 to about 100:0. After the tetraacid compound and the amines are reacted, the resulting polyamide may be filtered, washed and dried. The polyamide may be converted to a polyimide by heating the polyamide to a temperature above about 200° C. Either the polyamide or the polyimide may be used in a fluid separation membrane. In an embodiment, a dithiolene may be added to a polymer during a film casting process. The solvent may be removed from the resulting dithiolene polymer solution to provide a polymer film that has a dithiolene incorporated within the polymer.

The above-described fluid separation membranes may be used in any fluid separation apparatus known in the art. Generally, a fluid separation apparatus includes a body in which a fluid separation membrane is disposed. A fluid inlet may be positioned downstream from the fluid separation membrane. Two fluid outlets may be positioned upstream from the fluid inlet. A first fluid outlet may be positioned downstream from the fluid separation membrane. A second fluid separation membrane may be positioned upstream or downstream from the fluid separation membrane.

During use, a fluid stream that includes at least two components (e.g., a gas stream) may be introduced into the fluid separation apparatus via the fluid separation inlet. The fluid will then contact the fluid separation membrane. The fluid separation membrane may have a differential selectivity such that one of the components in the gas stream may pass through the fluid separation membrane at a rate that is faster than the rate at which the other component passes through. The faster permeating component passes through the gas separation membrane and flow out of the fluid separation apparatus via a fluid outlet. The gas that does not permeate through the membrane may exit the fluid separation apparatus via another fluid outlet. The fluid stream passing out of the fluid outlet upstream from the membrane may be recycled back into the fluid separation apparatus to improve the separation of the components and to maximize the yield of purified components.

BRIEF DESCRIPTION OF THE DRAWINGS

Advantages of the present invention may become apparent to those skilled in the art with the benefit of the following detailed description of the preferred embodiments and upon reference to the accompanying drawings in which.

Figure 1:
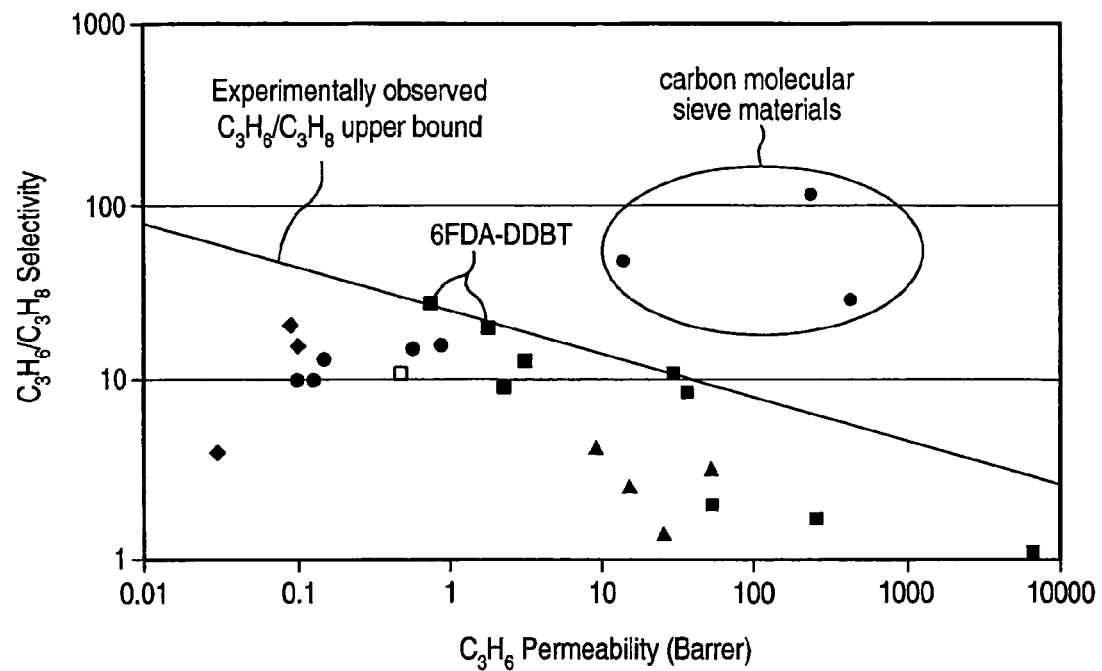
FIG. 1 depicts a $C_3H_6/C_3H_8$ upperbound tradeoff curve, based on available literature data.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Polyimide and poly (pyrrolone-imide) polymers are polymers derived from the condensation reaction of a tetraacid compound, a diamine and possibly a tetraamine. The resulting product is a polyamide. The remaining functional groups are then reacted during a thermal curing step to form the polyimide or poly (pyrrolone-imide). The polymerization may be conducted in an aprotic polar solvent capable of dissolving the monomers.

Tetraacid compounds, as used herein, include compounds that include at least four carboxylic acid groups and compounds that are derivatives of such compounds. Examples of tetraacid compounds include tetraacids, dianhydrides, and bis-ortho-ester-acid halides. Preferably, the tetraacid compound is an aromatic tetraacid or an aromatic tetraacid derivative. Aromatic tetraacid compounds tend to produce a rigid, thermally stable, productive and selective membrane material.

Tetraacids may be used to form the polyamide precursor polymer. The acid groups, in some embodiments, may be paired into ortho pairs that are separated by at least three atoms as shown in structures (1–3) below. The simplest compound to meet these requirements would be 1,2,4,5-benzene tetracarboxylic acid, shown as (1). The two ortho pairs are the 1,2 pair and the 4,5 pair, and three atoms lie between the carbons of the acid groups of non-ortho pairs. Other compounds include pyridine tetraacids (e.g., structure (2)) and pyrazine tetraacids (e.g., structure (3)).

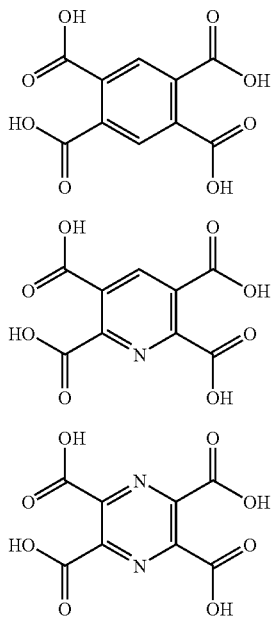

(1)

(2)

(3)

Tetraacids, however, may lack the reactivity to produce high molecular weight polymer. One way to increase the reactivity of the tetraacid compound is to convert the tetraacid into a dianhydride. Dianhydrides may be prepared from the corresponding tetraacids by heating to 230° C. in a vacuum or by refluxing the tetraacid with acetic anhydride. Examples of dianhydrides are shown as structures (4)–(6). The dianhydrides shown (4)–(6) are the dianhydrides that would be derived from the tetraacids (1)–(3) respectively.

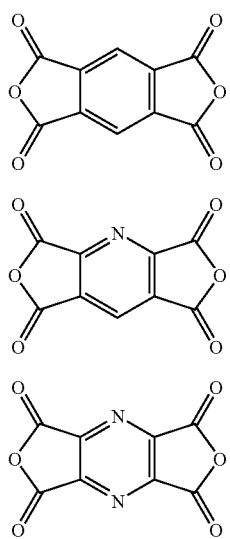

(4)

(5)

(6)

Naphthalene tetraacid derivatives may also be used. Naphthalene derivatives include carboxylic acid groups that may be either ortho-paired or para-paired. Naphthalene tetraacid derivatives include compounds having the general structure (7).

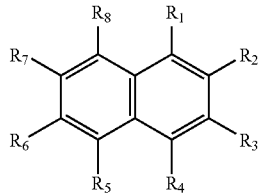

(7)

Ortho-paired and para-paired derivatives include compounds in which at least one of the pairs: $R_1$ and $R_2$; $R_2$ and $R_3$; $R_3$ and $R_4$; $R_1$ and $R_8$; and $R_1$ and $R_4$ is a pair of carboxylic acid groups; and at least one of the pairs: $R_5$ and $R_6$; $R_6$ and $R_7$; $R_7$ and $R_8$; $R_4$ and $R_5$; and $R_5$ and $R_8$ is a pair of carboxylic acid groups. An example of a para-paired naphthalene type monomer would be 1,4,5,8-naphthalene tetracarboxylic acid. Ortho-paired naphthalene tetraacid derivatives include 1,2,5,6-naphthalene tetracarboxylic acid (8) and 2,3,6,7-naphthalene tetracarboxylic acid (9).

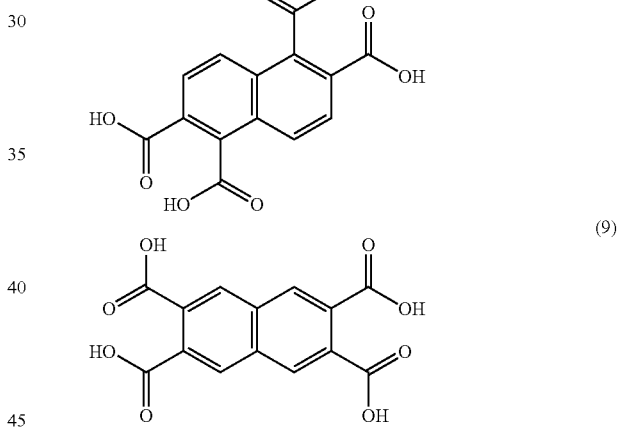

(8)

(9)

Naphthalene dianhydrides may also be used. Naphthalene dianhydrides may be prepared from the corresponding tetraacids by heating to 230° C. in a vacuum or by refluxing the tetraacid with acetic anhydride. Examples of naphthalene dianhydrides are shown as structures (10) and (11) which correspond to the dianhydrides that would be derived from the naphthalene tetracarboxylic acids (8) and (9) respectively.

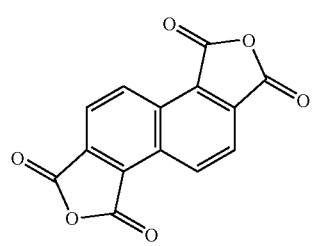

(10)

(11)

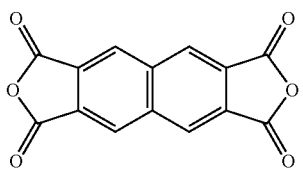

Other tetraacids may include aromatic bis-(ortho-dicarboxylic acids) and aromatic bis-(ortho-di-acid anhydrides). Generally, these compounds include a bis aromatic structure to which carboxylic acids and/or anhydrides are attached. Examples of these compounds include aromatic bis-(ortho-dicarboxylic acids) (12) and aromatic bis-(ortho-di-acid anhydrides) (13).

(12)

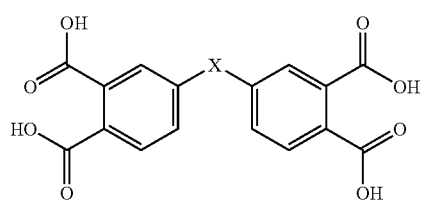

(13)

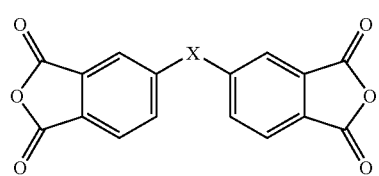

where X is a suitable linking group. Examples of linking groups include elemental linkages such as NH, O, or S. Other groups include $CH_2$, $C(O)$, $CH(CH_3)$, $C(CH_3)_2$, $C(CF_3)_2$, $C(CH_3)Ph$, $C(Ph)_2$, cyclohexyl, sulfoxide, sulfonate. A specific example of a compound having general structure (13), where X is $C(CF_3)_2$, is 4,4'-(hexafluoroisopropylidene) diphthalic anhydride (6FDA). Other linking groups may include compounds having the structures (14)–(17).

(14)

(15)

(16)

(17)

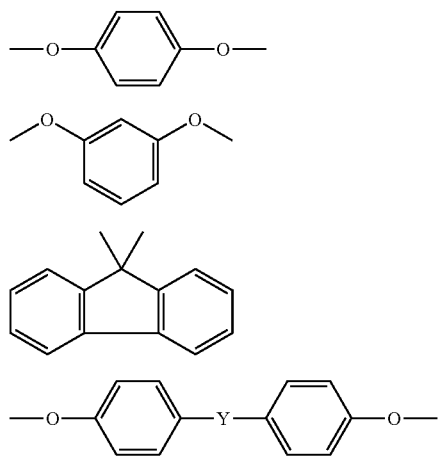

where Y is any of the other linking groups X. Alternatively, the linking group, X may represent a direct connection between the two aromatic groups such as depicted for the dianhydride (18).

(18)

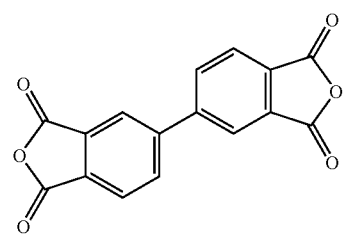

Another reactive tetraacid derivative is an acid chloride derivative. This type of compound may be prepared from any of the above described dianhydrides by reaction with an alcohol to form a bis-(ortho-acid-ester) followed by reaction to convert acid groups to acid halides. This method prepares a very reactive monomer, but this reactivity makes the monomer more water sensitive. Additionally, larger, more slowly diffusive side product alcohol groups are given off during the final cure of the polyamide to the polypyrrolone. With either the dianhydride or bis-ortho-ester-acid halide, preferably chloride, the functionality of the monomer is two, leading to linear polymer formation.

Tetraamines, as used herein, include compounds that include at least four amine groups. Preferably the tetraamine is an aromatic tetraamine. Aromatic tetraamine compounds tend to produce a rigid, thermally stable, productive and selective membrane material.

Tetraamines may be used to form the polyamide precursor polymer. The amine groups, in some embodiments, may be paired into ortho pairs that are separated by at least three atoms as shown in structures (18–20) below. The simplest compound to meet these requirements would be 1,2,4,5-tetraminobenzene (TAB), shown as (18). The two ortho pairs are the 1,2 pair and the 4,5 pair, and three atoms lie between the carbons of the acid groups of non-ortho pairs. Other compounds include pyridine tetraacids (e.g., structure (19)) and pyrazine tetraacids (e.g., structure (20)).

(18)

(19)

(20)

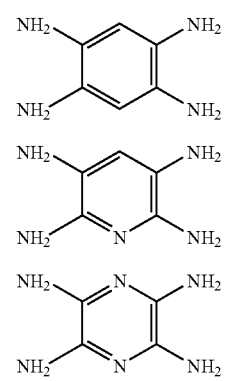

Naphthalene tetraamines may also be used. Naphthalene tetraamines include amine groups that may be either ortho-paired or para-paired. Naphthalene tetraamine derivatives include compounds having the general structure (21).

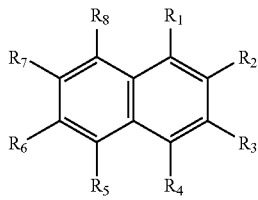

(21)

Ortho-paired and para-paired derivatives include compounds in which at least one of the pairs: $R_1$ and $R_2$; $R_2$ and $R_3$; $R_3$ and $R_4$; $R_1$ and $R_8$; and $R_1$ and $R_4$ is a pair os amine groups; and at least one of the pairs: $R_5$ and $R_6$; $R_6$ and $R_7$; $R_7$ and $R_8$; $R_4$ and $R_5$; and $R_5$ and $R_8$ is a pair of amine groups. An example of a para-paired naphthalene type monomer would be 1,4,5,8-tetraminonaphthalene (22). Ortho-paired naphthalene tetraamines include 1,2,5,6-tetraminonaphthalene (23) and 2,3,6,7-tetraaminonaphthalene (24).

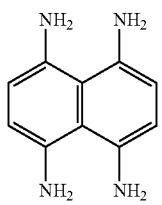

(22)

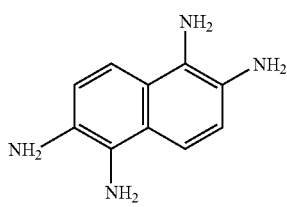

(23)

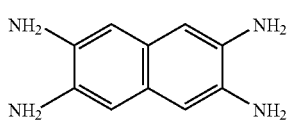

(24)

Other tetraacids may include aromatic bis-(ortho-diamines) (25). Generally, these compounds include a bis aromatic structure with amines attached to the aromatic groups. The linking group, X, may be the same as described above for the tetraacid derivatives.

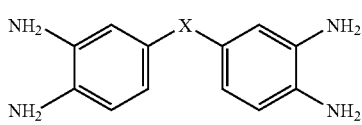

(25)

Other fused ring systems such as fluorene (26) and tetramethyl-spiro-biindane (27) may also serve as substrates for tetraamines (as depicted) or tetracarboxylic acid derivatives. However, all four of the acid or amino groups need not be attached to different ring, provided the four are split into ortho-pairs or para-pairs.

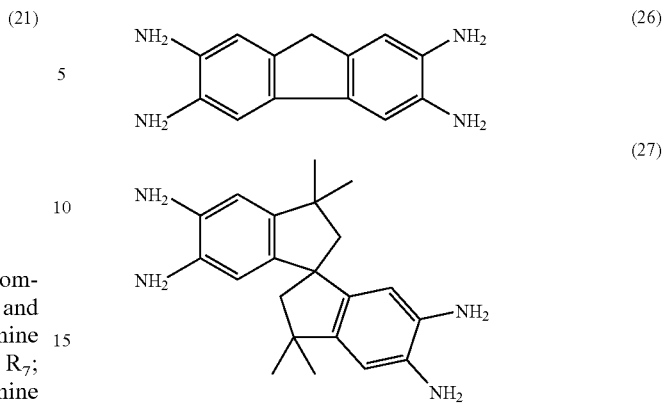

The tetraamines may be obtained either commercially, or by the reduction of a nitro compound, or may be synthesized in three steps from a bisphenol. The method for synthesis of tetraamine from bisphenol involves the nitration of the bisphenol, the nucleophilic exchange of the hydroxyl groups for amino groups, and reduction of the amino groups. The exchange of the hydroxyl groups for amino groups is similar to the procedure described in U.S. Pat. No. 2,894,988, which is incorporated herein by reference, for the conversion of nitro-cresols to nitro-toluidines. Spirobiindane-bisphenol, which serves as a basis for useful gas separating polycarbonates, can thus be converted to a tetraamine (12) for polypyrrolone synthesis of fluid separation materials. The synthesis of other tetraamines and tetraacids is described in U.S. Pat. No. 5,262,056 to Koros et al. which is incorporated herein by reference.

Diamines are, generally, molecules that include at least two amine groups. In one embodiment, aromatic diamines may be used. Aromatic diamines may be benzene based (28) or naphthalene based (29).

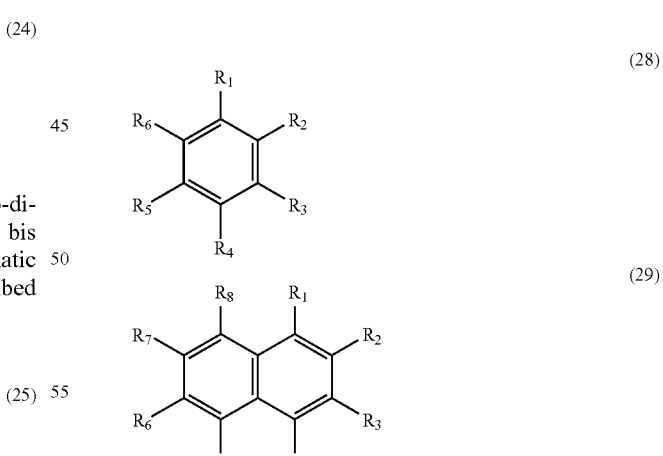

where, for benzene derivatives, meta or parasubstituted diamines may be used. As depicted in structure (28) $R_1$ and either $R_3$ or $R_4$ may be $NH_2$, where the remaining pendant groups are H or a $C_1$ to $C_{12}$ hydrocarbon. For naphthalene derivatives, at least two of $R_1$, $R_2$, $R_3$, $R_4$, $R_5$, $R_6$, $R_7$, and $R_8$ are $NH_2$ with the $NH_2$ groups being in an meta- or para orientation, the remaining pendant groups are H or a $C_1$ to $C_{12}$ hydrocarbon. Specific examples of aromatic diamines include 2,4,6-trimethyl-1,3-phenylene (DAM).

Other diamines may include bis-aromatic amines (41). Generally, these compounds include a bis aromatic structure with-amines attached to the aromatic groups. The linking group, X, may be the same as described above for the tetraacid derivatives.

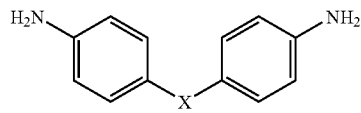
(41)

Specific examples of bis-aromatic amines include, but are not limited to, 4,4' (hexafluoroisopropylidene) dianiline (6FpDA) and 3,3'-dimethyl-4,4'-diaminophenyl (3,3'DMDB).

In one embodiment, a fluid separation membrane may be synthesized by the reaction of a tetraacid compound with an amine mixture that includes tetraamines and diamines. Polyimides are condensation polymers obtained from the reaction of aromatic dianhydrides with diamines followed by complete cyclization. Polypyrrolones are condensation polymers obtained from the reaction of aromatic dianhydrides and aromatic tetraamines followed by complete cyclization. The polymer obtained by the initial reaction of the monomers in an aprotic solvent is a soluble poly(amide amino acid), which can be thermally cyclized to form a polypyrrolone. A poly (pyrrolone-imide) may be synthesized in a similar manner. Initially a tetraacid compound is reacted with an amine mixture that includes tetraamines and diamines. In one embodiment the ratio of tetraamine to diamine in the amine mixture may be between about 5:95 to about 100:0. A small excess of the tetraacid compound may be used. Both the tetraamines and diamines condense with the tetraacid compound to form a polyamide. The polyamide may be thermally cyclized to form the poly (pyrrolone-imide). Thermal cyclization of an amide formed between the tetraacid compound and the tetraamine will lead to a pyrrolone linkage, while thermal cyclization of an amide formed between the tetraacid compound and the diamine will lead to imide linkages. The reaction of the tetraacid compound and the amine mixture may be performed in a polar aprotic solvent. Aprotic solvents, generally, are solvents that neither donate or accept protons. Examples of polar aprotic solvents include, but are not limited to dimethylformamide, n-methyl pyrrolidinone, dimethylacetamide, and dimethyl sulfoxide. One or all of the components may be dissolved in a polar aprotic solvent prior to reacting the components.

A base may be added to catalyze the formation of the polyamide. In an embodiment, a tertiary amine may be added to the amine mixture prior to the addition of the tetraacid compound. Suitable tertiary bases include, but are not limited to pyridine, pyrazine, triethylamine, diisopropyl ethyl amine, 1,5-diazabicyclo[4.3.0]non-5-ene ("DBN"), 1,4-diazabicyclo[2.2.2]octane, 1,8-diazabicyclo[5.4.0]undec-7-ene.

In one embodiment, the amine mixture may be dissolved in a polar aprotic solvent and placed in a reaction vessel. The tetraacid derivative may also be dissolved in a polar aprotic solvent and added to the amine mixture. The reaction may be conducted under an oxygen free atmosphere. An oxygen free atmosphere may be obtained by replacement of the ambient air in the reaction vessels with an inert gas such as helium, nitrogen, or a nobel gas (e.g., argon). Generally, the addition of the tetraacid compound to the amine mixture may cause an exothermic condensation reaction to occur. The rate of addition of the tetraacid derivative may be adjusted to control the temperature of the reaction. The resulting polyamide may be collected, filtered and dried to remove unreacted monomers and any base that may be present.

To convert the polyamide to a poly (pyrrolone-imide) the polyamide may be heated to cause further condensation of the amides. Condensation of the resulting amide may lead to either pyrrolone or imide linking groups. Thermal cyclocondensation may occur at temperatures above about 200° C. In one embodiment, the polyamide may be placed in a mold prior to thermal cyclocondensation such that the resulting poly (pyrrolone-imide) polymer has a shape that is complementary to the shape of the mold. The polyamide may be heated under an inert atmosphere or at a pressure below about 1.0 mmHg. Performing a thermal cyclocondensation under a vacuum may help to remove water formed during the condensation reaction and help accelerate the reaction rate. Thermal cyclocondensation is performed for a period of at least about one day, preferably two to three days. The polypyrrolone resulting from cyclization possesses a repeat unit with two benzene rings joined by two fused five membered rings, imparting a great degree of thermal and chemical resistance, strength and rigidity.

Either a polyimide, a polyamide or the poly (pyrrolone-imide) may be used as fluid separation membranes. Methods for forming and testing fluid separation membranes are described in detail in U.S. Pat. Nos. 5,262,056 and 6,602,415, both to Koros which are both incorporated herein by reference. The membranes of the present invention may be either composite or asymmetric membranes.

Figure 2:
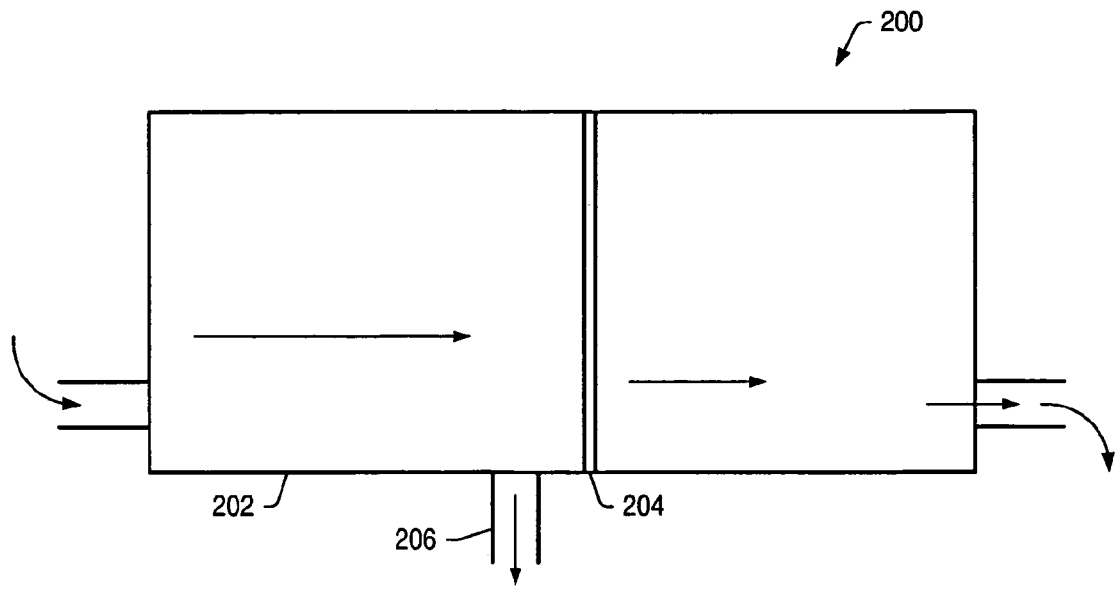
FIG. 2 depicts a fluid separation apparatus.

The above-described fluid separation membranes may be used in any fluid separation apparatus known in the art. A schematic of a fluid separation membrane is depicted in FIG. 2. Generally, a fluid separation apparatus 200 includes a body 202 in which a fluid separation membrane 204 is disposed. The fluid separation membrane 202 may be composed of any of the polymers described herein and formed by the methods described herein. A fluid inlet may be positioned downstream from the fluid separation membrane 204. Two fluid outlets may be positioned upstream from the fluid inlet. A first fluid outlet 206 may be positioned upstream from the fluid separation membrane. A second fluid separation membrane may be positioned upstream from the fluid separation membrane.

During use, a fluid stream that includes at least two components (e.g., a gas stream) may be introduced into the fluid separation apparatus 200 via the fluid separation inlet. The fluid will then contact the fluid separation membrane 204. The fluid separation membrane may have a differential selectivity such that one of the components in the gas stream may pass through the fluid separation membrane at a rate that is faster than the rate at which the other component passes through. Thus the faster permeating component will pass through the gas separation membrane and flow out of the fluid separation apparatus via an outlet. The gas that does not permeate through the membrane may exit the fluid separation apparatus via the outlet 206. The fluid stream passing out of the outlet 206 may be recycled back into the fluid separation apparatus to improve the separation of the components and to maximize the yield of purified components.

In an embodiment, dithiolenes may be added to a polymer mixture. The polymer may be formed as described herein. In an embodiment, the polymer may be formed by reacting a tetraacid and a diamine; a tetraacid and a tetraamine, or a tetraacid with a mixture of a tetraamine and a diamine. The polymer may be any polymer suitable to allow a particular dithiolene to be homogeneously dispersed. It may be necessary to use different polymers for different dithiolenes. The dithiolenes may be homogeneously dispersed within the polymer matrix. The resulting polymer dithiolene product may be used to form a fluid separation membrane as described herein. Addition of the dithiolene may increase the solubility selectivity of a fluid separation membrane. In an embodiment, a fluid separation membrane including dithiolenes may exhibit an olefin/paraffin solubility selectivity. A fluid separation membrane including dithiolenes may exhibit olefin/paraffin solubility selectivity of between about 1.1 to about 2.0. It is believed that the solubility selectivity of the membranes that incorporate dithiolene may be due to the ability of dithiolenes to reversibly complex with an olefin. The dithiolene may be resistant to poisoning by impurities. Poisoning within the context herein refers to decreasing the effectiveness of a compound or material as regards its intended purpose. Impurities may include any common impurities found in fluid streams that come into contact with a fluid separation membrane containing a dithiolene additive.

In an embodiment, the dithiolene may have the general structure (30):

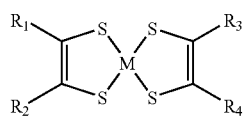

(30)

where M is a metal. Metals may include, but are not limited to nickel, platinum, and palladium. $R_1$, $R_2$, $R_3$, and $R_4$ may be each independently alkyl, H, $CH_3$, $CF_3$, $C_6H_4OCH_3$, CN, or aryl. $R_1$ and $R_2$ and/or $R_3$ and $R_4$ may combine to form at least one ring. The ring may be aromatic or nonaromatic. The ring may be substituted or nonsubstituted. Dithiolene (30) may be symmetric or asymmetric. In a particular example, $R_1$ and $R_2$ and $R_3$ and $R_4$ may combine to form substituted aromatic rings forming an overall asymmetric dithiolene (30). An asymmetric dithiolene may be a mixture of stereoisomers.

In an embodiment, dithiolene (30) may include a valence charge. The valence charge may be, for example, $-1$, or $-2$. Dithiolene (30) may include a counter ion. A counter ion may include any suitable counter ion known to one skilled in the art. A counter ion may be chosen for a number of different reasons based on what properties may be needed. For example, a counter ion may be chosen to increase the solubility of the entire complex. In one embodiment, the counter ion may have the structure (31):

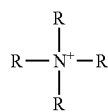

(31)

where each R is independently an alkyl or aromatic compound. In one embodiment, each R may be independently $C_2H_5$ or $C_4H_9$.

In an embodiment, dithiolene may have structure (32):

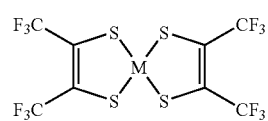

(32)

which is similar to structure (30), where $R_1$, $R_2$, $R_3$, and $R_4$ are $CF_3$. M is a metal such as nickel, platinum, or palladium.

In an embodiment, dithiolene may have structure (33):

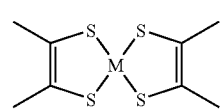

(33)

which is similar to structure (30), where $R_1$, $R_2$, $R_3$, and $R_4$ are $CF_3$. M is a metal such as nickel, platinum, or palladium.

In an embodiment, $R_1$, $R_2$, $R_3$, and $R_4$ are $C_6H_4OCH_3$. Each $OCH_3$ substituent separately may be positioned anywhere on the aromatic ring. In one embodiment, dithiolene may have structure (34):

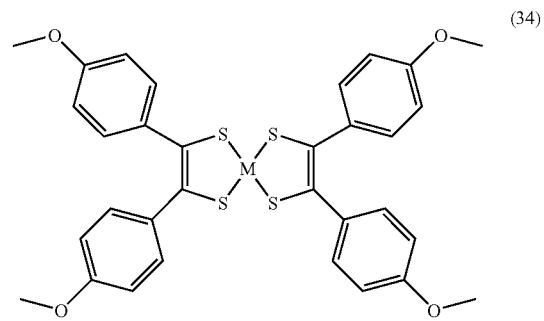

(34)

which is similar to structure (30), where $R_1$, $R_2$, $R_3$, and $R_4$ are $C_6H_4OCH_3$, with the methoxy substituent in the para position as depicted. M is a metal such as nickel, platinum, or palladium.

In an embodiment, dithiolene may have structure 35:

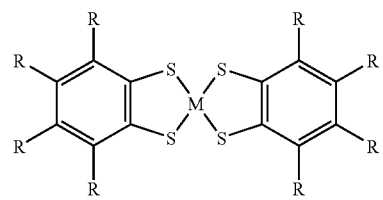

(35)

which is similar to structure 30, where $R_1$ and $R_2$, and $R_3$ and $R_4$ may combine to form a substituted aromatic ring. M is a metal such as nickel, platinum, or palladium.

In an embodiment, dithiolene has the structure 36:

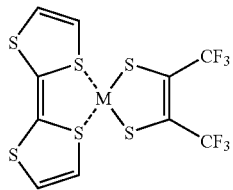
(36)

where $R_1$ and $R_2$ combine to form $C_6H_4S_4$, and $R_3$ and $R_4$ are $CF_3$. M is a metal such as nickel, platinum, or palladium.

A dithiolene may be dispersed in a polymer matrix as described herein. In an embodiment, a dithiolene may be dispersed in a polymer resulting from at least the reaction of a tretraacid and a diamine. The tetraacid may be dianhydrides such as (37) and/or (38):

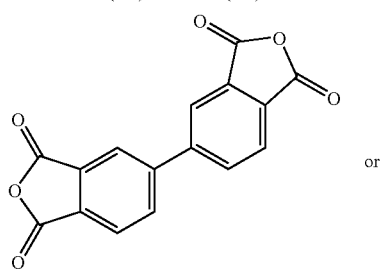
(37)

or

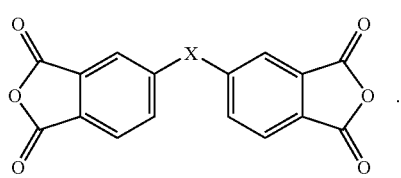
(38)

The diamine may have the structure (39):

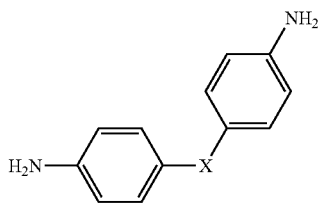
(39)

X may be, but is not limited to, a linking group such as $CH_2$, $C(O)$, $CH(CH_3)$, $C(CH_3)_2$, $C(CF_3)_2$, $C(CH_3)Ph$, $C(Ph)_2$, or cyclohexyl. A polymer matrix may be a polyimide polymer, a polyamide polymer, a polypyrrolone polymer, and/or a poly (pyrrolone-imide) polymer. A polyimide polymer may include recurring units having the structure (40):

X may be a linking group. Y may be another recurring unit. Recurring unit Y may be coupled to the aromatic ring in an ortho, meta, or para relation to the imide group.

EXAMPLES

Synthesis Procedure of 6FDA-6FpDA

All monomer materials were purified before the polymerization reaction. The 6FDA dianhydride and the 6FpDA diamine were each sublimed twice. The monomers were stored separately under high vacuum. For the synthesis of the polyimides in this study, chemical imidization was performed. In a moisture free flask with nitrogen inlet and magnetic stirrer, the diamine monomer was dissolved in N,N-dimethyl acetamide (DMAc) and the 6FDA dianhydride dissolved in DMAc was added dropwise at room temperature. The 20–25 wt % solution was stirred 6–8 h. Thereby high molecular polyamic acids were formed. The imidization was performed by the dehydration of the polyamic acids by adding a large excess of triethylamine and acetic anhydride to the reaction mixture and stirring 2–3 h at 323 K and 10–20 min at 373–383 K. After cooling to room temperature, the highly viscous reaction solution was slowly poured into methanol. The precipitated polyimide was homogenized in a blender; filtered and washed several times with fresh methanol. The obtained polyimide was dried 12 h under vacuum at room temperature and at least 24 h under vacuum at 523 K.

Film Casting Techniques

Films of the polymer materials were cast in a conventional manner in a fume hood. The appropriate amount of polymer was dissolved in a suitable solvent to form a 1–2 wt % solution. This solution was stirred for at least 20 minutes before filtering the solution with a 0.2 micron TEFLON syringe filter or alternatively filter paper from Fischer Scientific with medium porosity. The filtered solution was dispensed on a clean, level TEFLON dish or glass plate. The film was covered with a casting funnel to control the rate of solvent removal, and film formation generally occurred in under 8 hours. The films were then removed and placed in the vacuum oven at 100° C. for at least 24 hours to ensure complete solvent removal.

Dithiolene Experimental

A list of dithiolenes and their structures are presented in Table 1. In one experiment, the nine dithiolene complexes listed in Table 1, were evaluated for their reaction with $C_3H_6$. Experiments were conducted that included bubbling low pressure (e.g., atmospheric) $C_3H_6$ through a solution of the dithiolene complex in question. The results of these experiments are shown in Table 2. Some of the complexes were not soluble in toluene, but were soluble in dimethylacetamide. The goal of the experiment was to observe a color change over time, which would signal a chemical complexation with propylene. The only dithiolene material

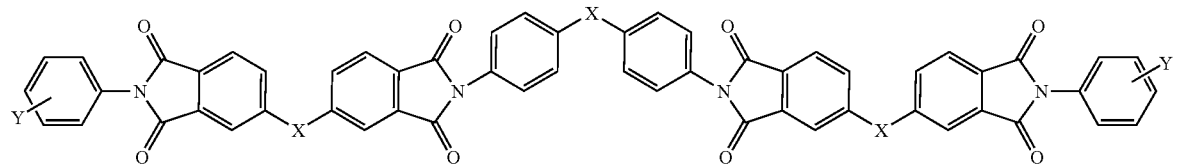
(40)

that underwent a significant change was complex #2, Ni[S₂C₂(CF₃)₂]₂, and this occurred in under 30 minutes. All other dithiolenes showed no color change under C₃H₆ bubbling, with the exception of dithiolene #5. This complex underwent a slight color change from yellow to light orange. The assumption from this would be that the olefin binding is very weak, as it appears the energy (reflected in the color) is not changed appreciably.

TABLE 1

Chemical Formula of dithiolene materials tested.

| # | Chemical Formula |
|---|---|
| 1 | Ni[S₂C₂(CH₃)₂]₂ |
| 2 | Ni[S₂C₂(CF₃)₂]₂ |
| 3 | Ni[S₂C₂(C₆H₄OCH₃)₂]₂ |
| 4 | [C₆H₄S₄]{Ni[S₂C₂(CF₃)₂]}⁻ |
| 5 | [N(n-C₄H₉)₄]{Ni[S₂C₂(CN)₂]₂}⁻ |
| 6 | [N(n-C₄H₉)₄]{Ni[S₂(C₆H₃CH₃)]₂}⁻ |
| 7 | [N(n-C₄H₉)₄]{Pt[S₂(C₆H₃CH₃)]₂}⁻ |
| 8 | [N(n-C₄H₉)₄]{Fe[S₂(C₆H₃CH₃)]₂}⁻ |
| 9 | [N(C₂H₅)₄]{Co[S₂(C₂(CN)₂]₂}⁻ |

TABLE 2

Results of C₃H₆ bubbling experiments for the 9 dithiolene samples examined.

| Dithiolene Complex | Solvent | Color | Time of C₃H₆ bubbling | Color change |
|---|---|---|---|---|
| #1 | Toluene | deep purple | 3 hrs | No change |
| #2 | Toluene | dark with purple tint | 30 minutes | yellowish - green |
| #3 | Toluene | dark forest green | 3 hrs | No change |
| #4 | Toluene | light yellow | 3 hrs | No change |
| #5 | DMAc | yellow | 3 hrs | light orange (very slight change) |
| #6 | Toluene | green with blue tint | 3 hrs | No change |
| #7 | Toluene | light blue | 3 hrs | No change |
| #8 | DMAc | light red | 3 hrs | No change |
| #9 | DMAc | yellow | 3 hrs | No change |

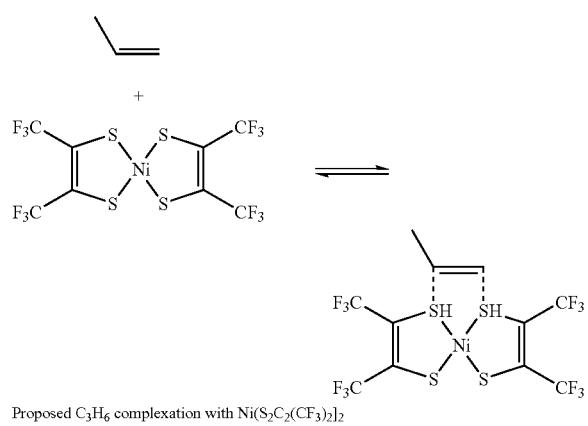

Proposed C₃H₆ complexation with Ni(S₂C₂(CF₃)₂)₂

Depicted above is the proposed method of complexation of propylene with a dithiolene. The observation that Ni[S₂C₂(CF₃)₂]₂ undergoes complexation with C₃H₆ is consistent with previous experiments in the literature.

In one embodiment, a film was prepared using 6FDA-6FpDA polyimide as the polymer matrix. The polyimide 6FDA-6FpDA was synthesized from a mixture of 6FDA and 6FpDA using the general methods described herein. It is believed that the presence of CF₃ groups in both the polymer and the dithiolene complex, Ni[S₂C₂(CF₃)₂]₂ should aid in miscibility of the polymer and the dithiolene. Films were cast from a mixture of 6FDA-6FpDA polymer and dithiolene on Teflon plates using techniques described herein with dicloromethane as the casting solvent. The films were then dried at 120° C. for at least 8 hours under vacuum. Homogenous films were formed that were also transparent dark green in epoxy on aluminum tape, compared to the pure 6FDA-6FpDA film, which is clear. After successfully achieving a polyimide/dithiolene homogenous blend, C₃H₆/C₃H₈ pure gas permeation and sorption experiments were conducted using the material 6FDA-6FpDA/Ni[S₂C₂(CF₃)₂]₂ (11 wt %).

Transport Results

C₃H₆/C₃H₈ Solubility Results

Figure 3:
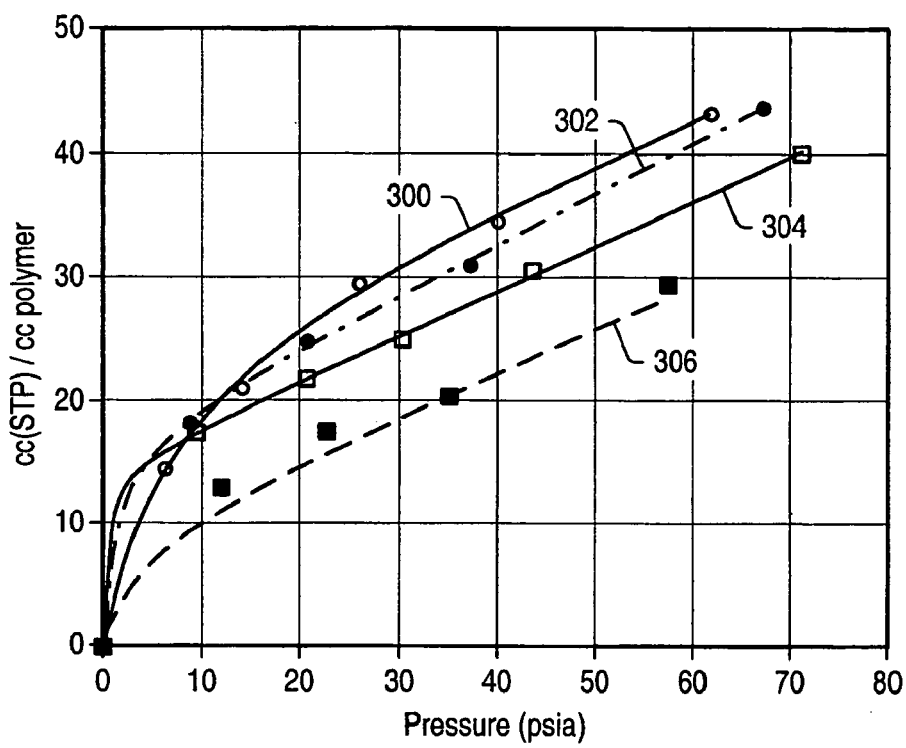
FIG. 3 depicts penetrant sorption in polymer films.

Initially pure gas C₃H₆/C₃H₈ sorption experiments were conducted for both the pure polymer, 6FDA-6FpDA, and the 6FDA-6FpDA/Ni[S₂C₂(CF₃)₂]₂ (11 wt %) blend, both processed using the same protocol. The results are shown in FIG. 3 on a plot of gas concentration versus equilibrium feed pressure. FIG. 3 depicts penetrant sorption in polymer films at 35° C. for C₃H₆ in ₆FDA-6FpDA/Ni[S₂C₂(CF₃)₂]₂ 302, C₃H₆ in 6FDA-6FpDA 300, C₃H₈ in 6FDA-6FpDA 304, C₃H6 in 6FDA-6FpDA/Ni[S₂C₂(CF₃)₂]₂ 306. These results were fit to the dual mode model describing gas sorption in both a Langmuir environment and a Henry's law environment:

$$S=(c/p)=k_D+[(C'_H b)/(1+bp)] \qquad (13)$$

where $k_D$ is the Henry's law constant, $C'_H$ is the Langmuir capacity constant, and b is the Langmuir affinity constant. The sorption isotherms are shown in FIG. 3. The results of the fitted parameters are shown in Table 3.

As shown in Table 3 there is a significant increase in b, the affinity constant, for C₃H₆ in the dithiolene containing material. Furthermore, there is also an increase in the Henry's law constant, $k_D$, for C₃H₆ within the material 6FDA-6FpDA/Ni[S₂C₂(CF₃)₂]₂, compared to the pure polyimide.

It would be expected that the $C'_H$ parameter would increase for C₃H₆ in the dithiolene-containing blend, and that $C'_H$ for C₃H₈ would remain relatively constant. Surprisingly, this is not what is observed. In both cases, (C₃H₆ and C₃H₈) the $C'_H$ parameter is depressed. This suggests that the dithiolene works to decrease the available defect free volume within the matrix. One possibility is that the dithiolene acts somewhat as a plasticizer, depressing the Tg of the matrix. Previous studies have shown correlations between the matrix Tg, and the $C'_H$ parameter.

Figure 4:
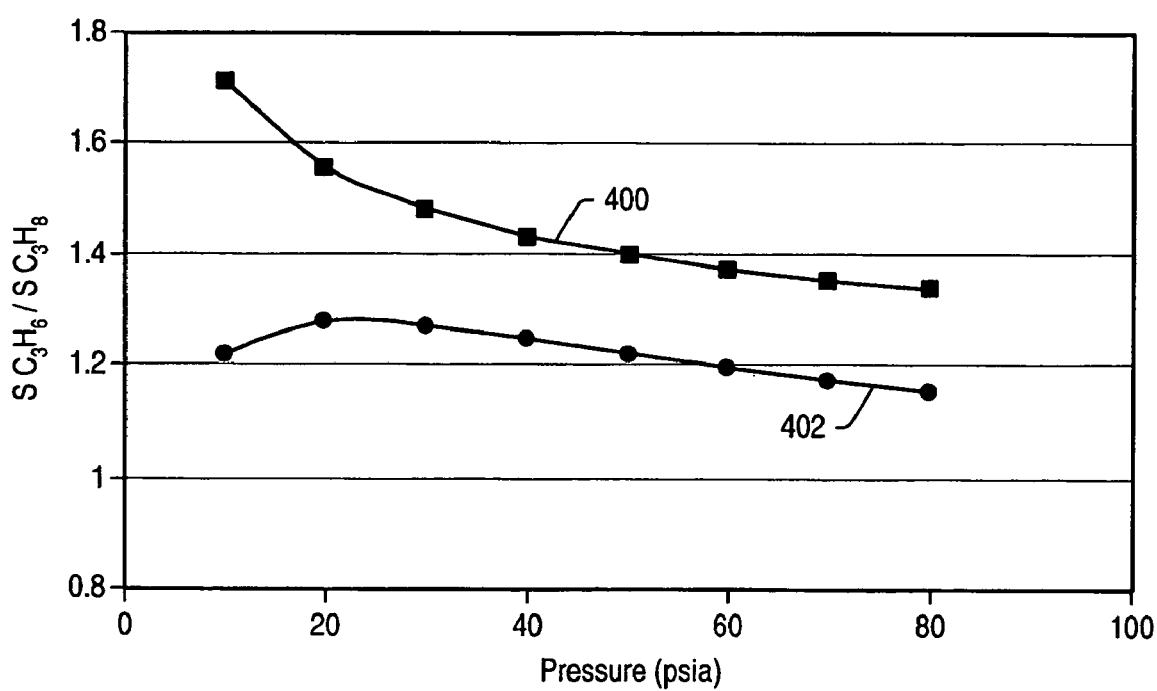
FIG. 4 depicts a comparison of $C_3H_6/C_3H_8$ solubility selectivity for 6FDA-6FpDA polyimide with dithiolene additive.

Using the dual mode data, it is possible to plot the pure gas C₃H₆/C₃H₈ solubility selectivity as a function of feed pressure for each of the materials studied (FIG. 4). As shown in FIG. 4, the solubility selectivity is improved at all pressures over the range studied. Line 400 depicts the solubility selectivity for 6FDA-6FpDA/dithiolene #2 (11%) in FIG. 4. Line 402 depicts the solubility selectivity for 6FDA-6FpDA in FIG. 4. The increase in the C₃H₆ affinity constant, b, provides a large increase in the overall solubility selectivity at low pressures. The increase in the C₃H₆ Henry's law constant maintains an increase in the solubility selectivity at higher pressures.

TABLE 3

Dual mode parameters for $C_3H_6/C_3H_8$ in 6FDA-6FpDA and 6FDA-6FpDA/Ni[$S_2C_2(CF_3)_2$]$_2$.

| Membrane Material | Gas | kD cc (STP)/cc polymer - psia | $C'_H$ cc (STP)/cc polymer | b psia-1 |
|---|---|---|---|---|
| 6FDA-6FpDA | $C_3H_6$ | 0.32 | 26.4 | 0.14 |
| 6FDA-6FpDA/Ni[$S_2C_2(CF_3)_2$]$_2$ | $C_3H_6$ | 0.40 | 17.2 | 0.70 |
| 6FDA-6FpDA | $C_3H_8$ | 0.36 | 14.6 | — |
| 6FDA-6FpDA/Ni[$S_2C_2(CF_3)_2$]$_2$ | $C_3H_8$ | 0.34 | 9.9 | 0.37 |

Figure 5:
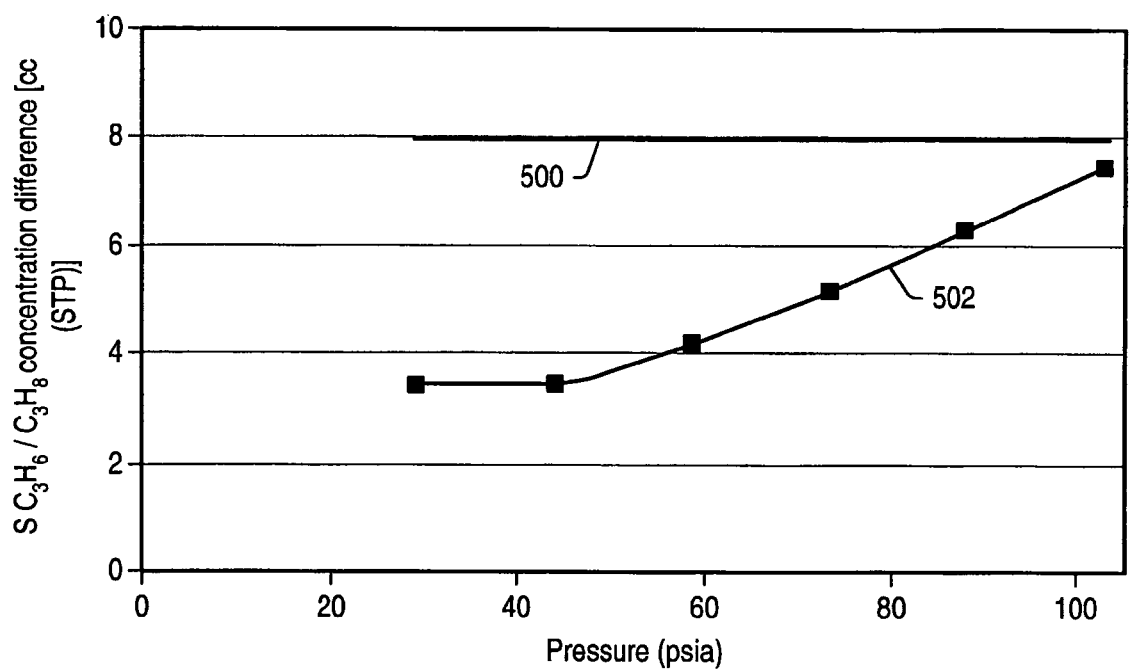
FIG. 5 depicts difference in $C_3H_6/C_3H_8$ concentration due to dithiolene additive.

FIG. 5 illustrates the difference in $C_3H_6/C_3H_8$ concentration due to the dithiolene additive. Concentration difference 502 increases with increased pressure, which is believed to indicate that the olefin is able to "access" more dithiolene molecules as the concentration increases in the polymer. Upper limit 500 represents the calculated maximum enhancement based on a mole balance assuming all dithiolene molecules form a complex. The experimental measurements approach this value as the pressure is increased.

REFERENCES

The following references, to the extent that they provide exemplary procedural or other information or details supplementary to those set forth herein, are specifically incorporated herein by reference.

Petropoulos, Quantitative Analysis of Gaseous Diffusion in Glassy Polymers, J. Polym. Sci, Part A-2, 8, 1970, 1797.

Vieth, Howell and Hsieh, Dual Sorption Theory, J. Memb. Sci, 1, 1976, 177.

Koros, Chan and Paul, Sorption and Transport of Various Gases in Polycarbonate, J. Memb. Sci., 2, 1977, 165.

Bondi, Physical Properties of Molecular Crystals, Liquid and Glasses, Wiley, New York, N.Y., 1968, chap. 14.

Van Krevelen, and Hoftyzer, Properties of Polymers, Their Estimation and Correlation with Chemical Structure, $2^{nd}$ Edition, Elsevier, New York, N.Y., 1976, chap. 4.

Scott et al., Polyimidazopyrrolone Reverse Osmosis Membranes, Polymer Letters, vol. 8, pp. 563–571 (1970).

Walker and Koros, Transport characterization of a polypyrrolone for gas separations, Journal of Membrane Science, 55:99–117 (1991).

Koros and Walker, Gas Separation Membrane Material Selection Criteria: Weakly and Strongly Interacting Feed Component Situations, Polymer Journal, vol. 23, no. 5, pp. 481–490 (1991).

Kim et al., "Relationship Between Gas Separation Properties and Chemical Structures in a Series of Aromatic Polyimides", J. Memb. Sci., 37 (1988a) 45.

Kim et al., "Advanced Gas Separation Membrane Materials: Rigid Aromatic Polyimides", J. Separation Science and Technology, 23 (1988b) 1611.

Kim, Ph.D. dissertation "Gas Sorption and Permeation in a Series of Aromatic Polyimides", 1988c.

Coleman, Ph.D. dissertation "Isomers of Fluorine Containing Polyimides for Gas Separation Membranes," 1992.

Tanaka, Taguchi, Jianquiang, Kita, and Okamoto, Permeation and separation properties of polyimide membranes to olefins and paraffins. *Journal of Membrane Science.* 1996, 121, 197–207.

Staudt-Bickel and Koros, Olefin/paraffin separation with 6FDA-based polyimide membranes, J. Membr. Sci. 170 (2000) 205.

Ilinitch, Semin, Chertova and Zamaraev, Novel polymeric membranes for separation of hydrocarbons, J. Membrane Sci., 82 (1993) 149.

Lee and Hwang, Separation of propylene and propane by polyimide hollow-fiber membrane module, J. Membrane Sci., 73 (1992) 37.

Ito and Hwang, Permeation of propane and propylene through cellulosic polymer membranes, J. Apply. Polym. Sci., (1989) 483.

Steel, Carbon Membranes for Challenging Gas Separations, Ph.D. Dissertation, The University of Texas at Austin, 2000.

L. M. Robeson, Correlation of Separation Factor Versus Permeability for Polymeric Membranes, J. Memb. Sci., 62, 1991, 165.

C. M. Zimmerman, Advanced Gas Separation Membrane Materials: Hyper Rigid Polymers and Molecular Sieve-Polymer Mixed Matrices, Ph.D. Dissertation, The University of Texas at Austin, 1998.

Walker, Synthesis and Characterization of Polypyrrolones for Gas Separation Membranes, Ph. D. Dissertation, The University of Texas at Austin, 1993.

Bell and Jewell, Synthesis and Properties of Polyimidazopyrrolones, J. Polym. Sci., Polym. Chem. Ed., 5 (1967) 3043.

B. D. Freeman, Basis of Permeability/Selectivity Tradeoff Relation in Polymeric Gas Separation Membranes, Macromolecules 32 (1999) 375–380.

I. Pinnau and L. G. Toy, Solid polymer electrolyte composite membranes for olefin/paraffin separation, J. Membr. Sci. 184 (2001) 39–48.

Y. S. Park, J. Won and Y. S. Kang, Facilitated transport of olefin through solid PAAm and PAAm-graft composite membranes with silver ions, J. Membr. Sci. 183 (2001) 163–170.

S. Bai, S. Sridhar and A. A. Khan, Metal-ion mediated separation of propylene from propane using PPO membranes, J. Membr. Sci. 147 (1998) 131–139.

I. Pinnau and L. G. Toy, Solid polymer electrolyte composite membranes for olefin/paraffin separation, J. Membr. Sci. 184 (2001) 39–48.

K. Wang and E. I. Stiefel, Toward Separation and Purification of Olefins Using Dithiolene Complexes: An Electrochemical Approach, Science 291 (2001) 106.

D. C. Olson, V. P. Mayweg and G. N. Schrauzer, Polarographic Study of Coordination Compounds with Delocalized Ground States. Substituent Effects in Bis- and Tris-dithiodiketone Complexes of Transition Metals, J. Am. Chem. Soc. 88 (1966) 4876–4882.

W. J. Koros and D. R. Paul, $CO_2$ Sorption in Poly(Ethylene-Terephthalate) above and Below Glass-Transition, J. Polym. Sci. Pt. B-Polym. Phys. 16 (1978) 1947–1963.

A. Shimazu, T. Miyazaki, M. Maeda and K. Ikeda, Relationships between the chemical structures and the solubility, diffusivity, and permselectivity of propylene and propane in 6FDA-based polyimides, J. Polym. Sci. Pt. B-Polym. Phys. 38 (2000) 2525–2536.

Shimazu, T. Miyazaki, T. Matsushita, M. Maeda and K. Ikeda, Relationships between chemical structures and solubility, diffusivity, and permselectivity of 1,3-butadiene and n-butane in 6FDA-based polyimides, J. Polym. Sci. Pt. B-Polym. Phys. 37 (1999) 2941–2949.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A fluid separation membrane for separating one or more components from a fluid, the fluid comprising two or more components, wherein the fluid separation membrane comprises at least one polymer and at least one dithiolene having the structure:

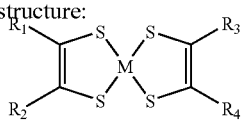

where M is a metal, wherein $R_1$, $R_2$, $R_3$, and $R_4$ are each independently alkyl, $CH_3$, $CF_3$, $C_6H_4OCH_3$, CN, or where $R_1$ and $R_2$ and/or $R_3$ and $R_4$ combine to form at least one ring.

2. The fluid separation membrane of claim 1, wherein the membrane exhibits an olefin/paraffin solubility selectivity.

3. The fluid separation membrane of claim 1, wherein the membrane exhibits an olefin/paraffin solubility selectivity of 1.1 to 2.0.

4. The fluid separation membrane of claim 1, wherein at least one dithiolene is resistant to poisoning by impurities.

5. The fluid separation membrane of claim 1, wherein the metal is Ni, Pd, or Pt.

6. The fluid separation membrane of claim 1, wherein at least one dithiolene further comprises a valence charge, and wherein the valence charge is 0, −1, or −2.

7. The fluid separation membrane of claim 1, wherein at least one dithiolene further comprises a valence charge, wherein the valence charge is −1 or −2, and wherein the dithiolene comprises a counter ion.

8. The fluid separation membrane of claim 1, wherein at least one dithiolene further comprises a valence charge, wherein the valence charge is −1 or −2, and wherein the dithiolene comprises at least one counter ion having the structure:

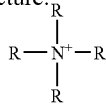

where each R is independently an alkyl or aromatic compound.

9. The fluid separation membrane of claim 1, wherein at least one dithiolene further comprises a valence charge, wherein the valence charge is −1 or −2, and wherein the dithiolene comprises at least one counter ion having the structure:

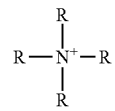

where each R is independently $C_2H_5$ or $C_4H_9$.

10. The fluid separation membrane of claim 1, wherein at least one dithiolene is capable of complexing with an olefin.

11. The fluid separation membrane of claim 1, wherein the fluid comprises a liquid.

12. The fluid separation membrane of claim 1, wherein the fluid comprises a gas stream.

13. The fluid separation membrane of claim 1, wherein the fluid comprises a gas stream, and wherein the gas stream comprises a hydrocarbon.

14. The fluid separation membrane of claim 1, wherein $R_1$, $R_2$, $R_3$, and $R_4$ are $CH_3$, at least one dithiolene having the structure:

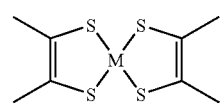

15. The fluid separation membrane of claim 1, wherein $R_1$, $R_2$, $R_3$, and $R_4$ are $CF_3$, at least one dithiolene having the structure:

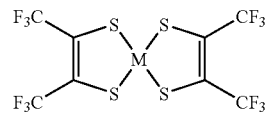

16. The fluid separation membrane of claim 1, wherein $R_1$, $R_2$, $R_3$, and $R_4$ are $C_6H_4OCH_3$, at least one dithiolene having the structure:

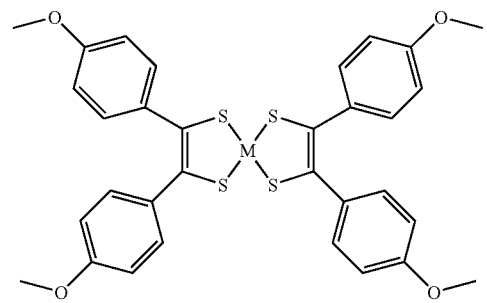

17. The fluid separation membrane of claim 1, wherein $R_1$ and $R_2$ combine to form $C_6H_3CH_3$, and wherein $R_3$ and $R_4$ combine to form $C_6H_3CH_3$, at least one dithiolene having the structure:

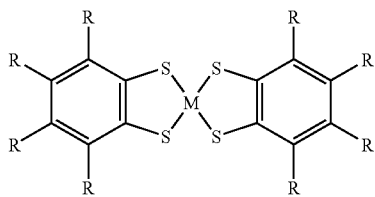

where each R is independently H, CH$_3$, alky, or aryl.

18. The fluid separation membrane of claim 1, wherein R$_1$ and R$_2$ combine to form C$_6$H$_4$S$_4$, and wherein R$_3$ and R$_4$ are CF$_3$, at least one dithiolene having the structure:

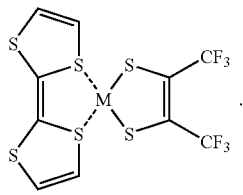

19. The fluid separation membrane of claim 1, wherein at least one polymer comprises the reaction product of a tetraacid compound and a diamine.

20. The fluid separation membrane of claim 1, wherein at least one polymer comprises the reaction product of a tetraacid compound and a diamine, wherein the tetraacid compound comprises an aromatic dianhydride having the structure:

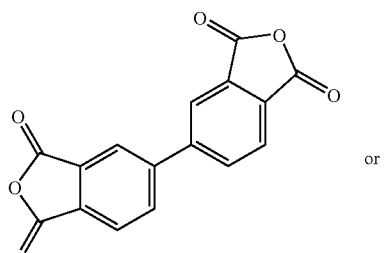

or

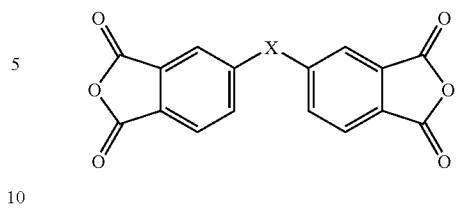

wherein the diamine having the structure:

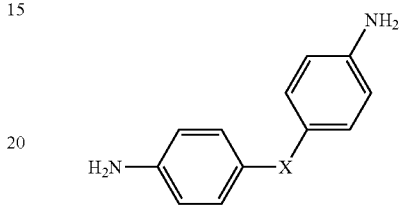

and wherein each X is independently CH$_2$, C(O), CH(CH$_3$), C(CH$_3$)$_2$, C(CF$_3$)$_2$, C(CH$_3$)Ph, C(Ph)$_2$, or cyclohexyl.

21. The fluid separation membrane of claim 1, wherein at least one polymer comprises a polyimide polymer, a polyamide polymer, a polypyrrolone polymer, or a poly (pyrrolone-imide) polymer.

22. The fluid separation membrane of claim 1, wherein at least one polymer comprises a polyimide polymer, wherein the polyimide polymer comprises recurring units, a portion of the recurring units having the structure:

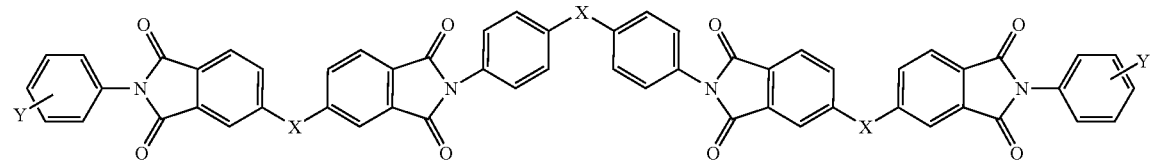

where X is a linking group, and Y is another recurring unit, where recurring unit Y is coupled to the aromatic ring in an ortho, meta, or para relation to the imide group.

23. A fluid separation membrane for separating one or more components from a fluid, the fluid comprising two or more components, wherein the fluid separation membrane comprises at least one polymer and at least one dithiolene having the structure:

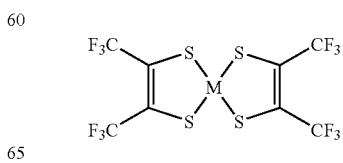

where M is a metal.

24. The fluid separation membrane of claim 23, wherein the membrane exhibits an olefin/paraffin solubility selectivity.

25. The fluid separation membrane of claim 23, wherein the membrane exhibits an olefin/paraffin solubility selectivity of 1.1 to 2.0.

26. The fluid separation membrane of claim 23, wherein the metal is Ni, Pd, or Pt.

27. The fluid separation membrane of claim 23, wherein at least one dithiolene further comprises a valence charge, and wherein the valence charge is 0, −1, or −2.

28. The fluid separation membrane of claim 23, wherein at least one dithiolene further comprises a valence charge, wherein the valence charge is −1 or −2, and wherein the dithiolene comprises a counter ion.

29. The fluid separation membrane of claim 23, wherein at least one dithiolene further comprises a valence charge, wherein the valence charge is −1 or −2, and wherein the dithiolene comprises at least one counter ion having the structure:

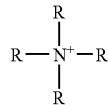

where each R is independently an alkyl or aromatic compound.

30. The fluid separation membrane of claim 23, wherein at least one dithiolene further comprises a valence charge, wherein the valence charge is −1 or −2, and wherein the dithiolene comprises at least one counter ion having the structure:

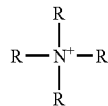

where each R is independently $C_2H_5$ or $C_4H_9$.

31. The fluid separation membrane of claim 23, wherein at least one dithiolene is capable of complexing with an olefin.

32. The fluid separation membrane of claim 23, wherein the fluid comprises a liquid.

33. The fluid separation membrane of claim 23, wherein the fluid comprises a gas stream.

34. The fluid separation membrane of claim 23, wherein the fluid comprises a gas stream, and wherein the gas stream comprises a hydrocarbon.

35. The fluid separation membrane of claim 23, wherein at least one polymer comprises the reaction product of a tetraacid compound and a diamine.

36. The fluid separation membrane of claim 23, wherein at least one polymer comprises the reaction product of a tetraacid compound and a diamine, wherein the tetraacid compound comprises an aromatic dianhydride having the structure:

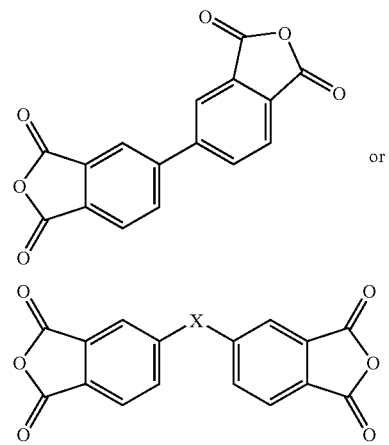

wherein the diamine having the structure:

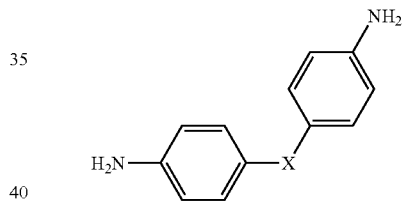

and wherein each X is independently $CH_2$, $C(O)$, $CH(CH_3)$, $C(CH_3)_2$, $C(CF_3)_2$, $C(CH_3)Ph$, $C(Ph)_2$, or cyclohexyl.

37. The fluid separation membrane of claim 23, wherein at least one polymer comprises a polyimide polymer, a polyamide polymer, a polypyrrolone polymer, or a poly(pyrrolone-imide) polymer.

38. The fluid separation membrane of claim 23, wherein at least one polymer comprises a polyimide polymer, wherein the polyimide polymer comprises recurring units, a portion of the recurring units having the structure:

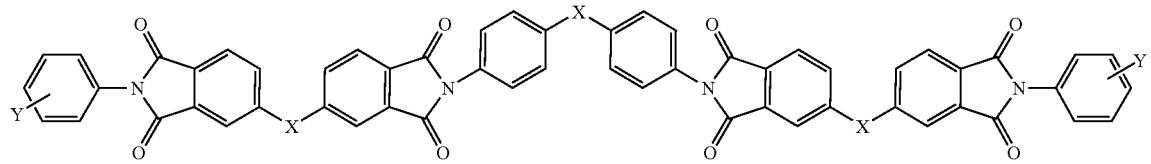

where X is a linking group, and Y is another recurring unit, where recurring unit Y is coupled to the aromatic ring in an ortho, meta, or para relation to the imide group.

39. A method of preparing a fluid separation membrane for separating one or more components from a fluid, the fluid comprising two or more components, comprising adding at least one dithiolene to at least one polymer, the dithiolene having the structure:

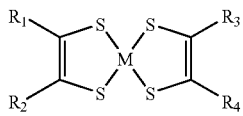

where M is a metal, wherein $R_1$, $R_2$, $R_3$, and $R_4$ are each independently alkyl, $CH_3$, $CF_3$, $C_6H_4OCH_3$, CN, or where $R_1$ and $R_2$ and/or $R_3$ and $R_4$ combine to form at least one ring.

40. A method of separating one or more components from a fluid, the fluid comprising two or more components, comprising bringing the fluid stream into contact with a face of a fluid separation membrane, the fluid separation membrane comprising at least one polymer and at least one dithiolene having the structure:

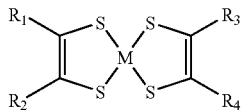

where M is a metal, wherein $R_1$, $R_2$, $R_3$, and $R_4$ are each independently alkyl, $CH_3$, $CF_3$, $C_6H_4OCH_3$, CN, or where $R_1$ and $R_2$ and/or $R_3$ and $R_4$ combine to form at least one ring.

41. An apparatus for separating one or more components from a fluid, the fluid comprising two or more components, comprising:

a body;

a fluid separation membrane disposed within the body, the fluid separation membrane comprising at least one polymer and at least one dithiolene having the structure:

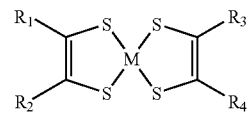

where M is a metal, wherein $R_1$, $R_2$, $R_3$, and $R_4$ are each independently alkyl, $CH_3$, $CF_3$, $C_6H_4OCH_3$, CN, or where $R_1$ and $R_2$ and/or $R_3$ and $R_4$ combine to form at least one ring;

a fluid stream inlet coupled to the body downstream from the fluid separation membrane;

a first fluid stream outlet positioned upstream from the fluid stream inlet and down stream from the fluid separation membrane; and a second fluid stream outlet positioned downstream from the fluid separation membrane.

* * * * *